US010945806B2

(12) United States Patent
Wall et al.

(10) Patent No.: US 10,945,806 B2
(45) Date of Patent: Mar. 16, 2021

(54) SURGICAL GUIDE AND METHODS OF USE

(71) Applicant: Warsaw Orthopedic, Inc., Warsaw, IN (US)

(72) Inventors: Daniel Paxton Wall, Cordova, TN (US); Richard Quinn Brown, Collierville, TN (US); Adam Glaser, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 162 days.

(21) Appl. No.: 16/124,801

(22) Filed: Sep. 7, 2018

(65) Prior Publication Data
US 2020/0078068 A1 Mar. 12, 2020

(51) Int. Cl.
*A61B 90/11* (2016.01)
*A61B 34/30* (2016.01)
*A61B 17/17* (2006.01)
*A61B 17/90* (2006.01)
*A61B 17/88* (2006.01)
*A61B 34/20* (2016.01)
*A61C 1/14* (2006.01)
(Continued)

(52) U.S. Cl.
CPC .............. *A61B 90/11* (2016.02); *A61B 17/17* (2013.01); *A61B 17/1757* (2013.01); *A61B 17/8886* (2013.01); *A61B 34/20* (2016.02); *A61B 34/30* (2016.02); *A61B 90/57* (2016.02); *A61C 1/14* (2013.01); *A61B 2017/00477* (2013.01); *A61B 2017/320052* (2013.01); *A61B 2017/90* (2013.01); *A61B 2034/305* (2016.02)

(58) Field of Classification Search
CPC ...... A61B 2017/00477; A61B 17/1633; A61B 17/17; A61B 17/8875; A61B 2017/90; A61B 2034/305; A61B 17/0482; A61B 2017/320052; A61B 90/11; A61C 1/14; A61C 3/04; B25B 5/04; B25H 1/0021; B25H 1/0078; B25H 1/10
See application file for complete search history.

(56) References Cited

U.S. PATENT DOCUMENTS 7,364,536 B2 * 4/2008 Cappellini ......... A63B 21/0724
482/106
7,549,998 B2 6/2009 Braun
(Continued)

FOREIGN PATENT DOCUMENTS

EP 0908277 A2 * 4/1999 ............... B25H 1/10
JP 2017205495 A 11/2017
WO 2016087539 A2 6/2019

OTHER PUBLICATIONS

International Search Report and Written Opinion of the International Searching Authority, Korean Patent Office, PCT/US2019/048444, dated Dec. 17, 2019.

*Primary Examiner* — Larry E Waggle, Jr.
(74) *Attorney, Agent, or Firm* — Sorell, Lenna & Schmidt, LLP

(57) ABSTRACT

A surgical guide comprising a body including an inner surface that defines a cavity configured for disposal of a surgical instrument. The body further defining an opening communicating with the cavity. A connector disposable with the opening and engageable with a surgical robot. A release is engageable with the connector. Systems, spinal constructs, implants and surgical instruments are disclosed.

17 Claims, 7 Drawing Sheets

(51) Int. Cl.
*A61B 90/57* (2016.01)
*A61B 17/00* (2006.01)
*A61B 17/32* (2006.01)

(56) References Cited

U.S. PATENT DOCUMENTS

| | | |
|---|---|---|
| 7,976,549 B2 | 7/2011 | Dye et al. |
| 8,182,491 B2 | 5/2012 | Selover et al. |
| 8,771,282 B2 | 7/2014 | Blain et al. |
| 8,827,216 B2 * | 9/2014 | Brown ................ B25H 1/0021 |
| | | 248/124.1 |
| 8,999,892 B2 | 4/2015 | Quaghebeur |
| 2015/0305817 A1 * | 10/2015 | Kostrzewski .......... A61B 34/70 |
| | | 606/130 |
| 2015/0335368 A1 * | 11/2015 | Auger ................... F16B 23/003 |
| | | 606/319 |
| 2016/0000512 A1 | 1/2016 | Gombert et al. |
| 2020/0085500 A1 * | 3/2020 | Dace ................. A61B 17/7032 |

\* cited by examiner

SURGICAL GUIDE AND METHODS OF USE

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, one or more rods and bone fasteners can be delivered to a surgical site. Surgical instruments are employed, for example, to engage the fasteners for attachment to the exterior of two or more vertebral members. This disclosure describes an improvement over these prior technologies.

SUMMARY

In one embodiment, a surgical guide is provided. The surgical guide comprises a body including an inner surface that defines a cavity configured for disposal of a surgical instrument. The body further defines an opening communicating with the cavity. A connector is disposable with the opening and engageable with a surgical robot. A release is engageable with the connector. In some embodiments, systems, spinal constructs, implants and surgical instruments are disclosed.

In one embodiment, the surgical guide comprises a robotic arm including an inner surface that defines a channel configured for disposal of a surgical instrument. The robotic arm further defines an opening communicating with the channel. A screw is disposable with the opening and engageable with a surgical robot. A rotatable wheel is engageable with the screw.

In one embodiment, the surgical guide comprises a body including an inner surface that defines a cavity configured for disposal of a surgical instrument. The body further defines an opening communicating with the cavity and a slot in communication with the opening. A connector is disposable with the opening and engageable with a surgical robot. A release is disposable with the slot and engageable with the connector.

BRIEF DESCRIPTION OF THE DRAWINGS

The present disclosure will become more readily apparent from the specific description accompanied by the following drawings, in which.

DETAILED DESCRIPTION

Figure 1:
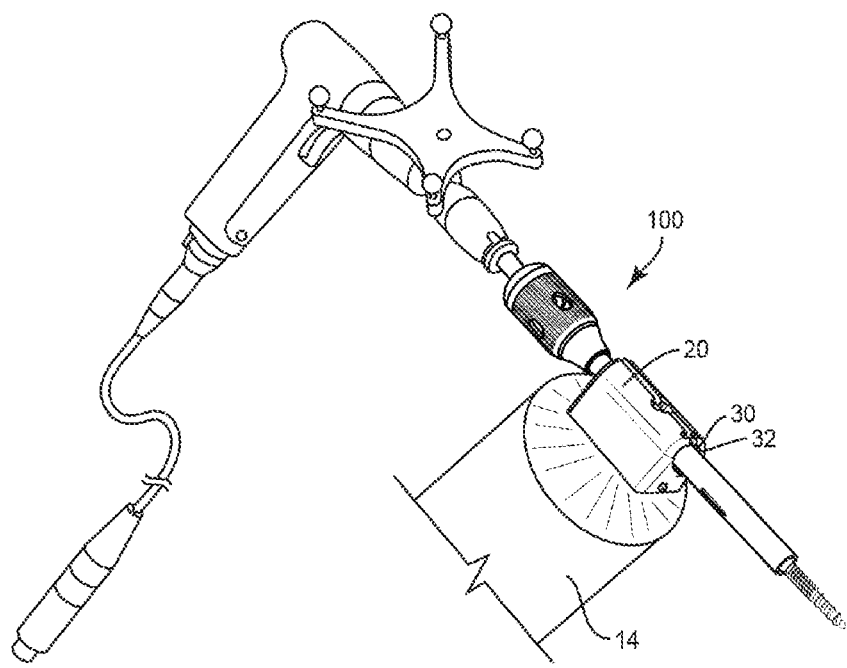
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system comprises an image guided, robot assisted spinal implant system. In some embodiments, the systems and methods of the present disclosure comprise surgical robotic guidance, surgical navigation and medical devices including surgical instruments and implants that are employed with a surgical treatment, as described herein, for example, with a cervical, thoracic, lumbar and/or sacral region of a spine.

In some embodiments, the present surgical system comprises a surgical guide connectable with a surgical robot, surgical robotic guidance, surgical navigation and/or medical devices. In some embodiments, the present surgical system comprises a surgical guide including a release, for example, a rescue mechanism to release a surgical instrument that is fixed, frictionally fixed, stuck, galled and/or jammed in the surgical guide. In some embodiments, the release enables the surgical guide to be removed from the surgical robot. In some embodiments, the release configuration allows the surgical guide to be replaced with a new surgical guide and/or reduces component manipulation time during a surgical procedure.

In some embodiments, the present surgical system comprises a surgical guide including a release, for example, a rescue wheel for a robotic arm guide. In some embodiments, the surgical guide includes a rescue wheel that can be manipulated with a surgical driver or similar surgical instrument. In some embodiments, the surgical guide is retained/removed by a surgical driver that is accessed from a front of the surgical guide through an opening. In some embodiments, the surgical guide can include a clamp screw to retain a surgical instrument with the guide. In the instance of a surgical instrument being fixed, frictionally fixed, stuck, galled and/or jammed with an inner surface of the surgical guide, the clamp screw may not be accessible from a conventional access, trajectory and/or front side of the surgical guide to free the surgical instrument. In some embodiments, the release of the surgical guide allows the clamp screw to be backed out to free the surgical instrument although there is not conventional access to the clamp screw. In some embodiments, this configuration facilitates removal of the surgical guide from a surgical robot if a surgical instrument is fixed, frictionally fixed, stuck, galled and/or jammed in the surgical guide.

In some embodiments, the present surgical system comprises a surgical guide including a release designed to be disposed in a flush orientation with an outer surface of the surgical guide. In some embodiments, the surgical guide includes a release that is actuated by a surgical instrument that can fit inside slots of a surgical guide, such as a surgical driver.

In some embodiments, the present surgical system comprises a surgical guide including a rescue wheel that can be manipulated with a surgical driver or similar instrument. In some embodiments, this configuration allows a connector, for example, a clamp screw to be released and/or backed out when there is no access to the clamp screw. In some embodiments, the surgical guide includes through slots for disposal of the rescue wheel.

In some embodiments, the surgical guide includes an opening for disposal of a connecting screw that can be accessed from a front trajectory relative to the surgical guide. In some embodiments, the opening includes a pocket so that screw travel is limited and the screw maintains engagement of the screw to the rescue wheel. In some embodiments, the opening provides a range of movement of the screw in the opening between a minimum wheel engagement and a full wheel engagement. In some embodiments, the screw protrudes from an outer surface of the surgical guide a selected distance, for example, 1 millimeter, for example, from a rear surface of the surgical guide. In some embodiments, an outside diameter of the rescue wheel is flush to an outside surface of the surgical guide. In some embodiments, the screw includes a head having at least one flat surface. In some embodiments, the rescue wheel includes a mating surface that engages a mating surface of the screw. In some embodiments, the mating surfaces include flats, as described herein.

In some embodiments, the present surgical system is employed with a method of performing robotically-assisted spinal surgery. In some embodiments, the method includes the step of delivering posterior spinal instrumentation through robotic-assisted trajectory alignment tools. In some embodiments, the present surgical system and method includes surgical robotic guidance having robotic software that performs registration of a patient anatomy to a three dimensional working space of a robot.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including surgical robotic guidance, surgical navigation, surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-8, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth and/or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, one or more of the components of surgical system 10 are configured for engagement with existing spinal constructs, which may include spinal implants such as one or more rods, fasteners, plates and connectors. In some embodiments, the spinal constructs can be attached with vertebrae in a revision surgery to manipulate tissue and/or correct a spinal disorder, as described herein.

Surgical system 10 includes a surgical robotic guidance system having a surgical guide, such as, for example, an end effector 20 connected to a robotic arm 14. The surgical robotic guidance system is employed with one or a plurality of surgical instruments for manipulating vertebral tissue, and for delivering and introducing components of spinal constructs for engagement with the vertebral tissue. End effector 20 includes a release, for example, a rescue mechanism configured to facilitate removal of end effector 20 from robotic arm 14 if a surgical instrument and/or spinal construct becomes fixed, frictionally fixed, stuck, galled and/or jammed within end effector 20.

Figure 2:
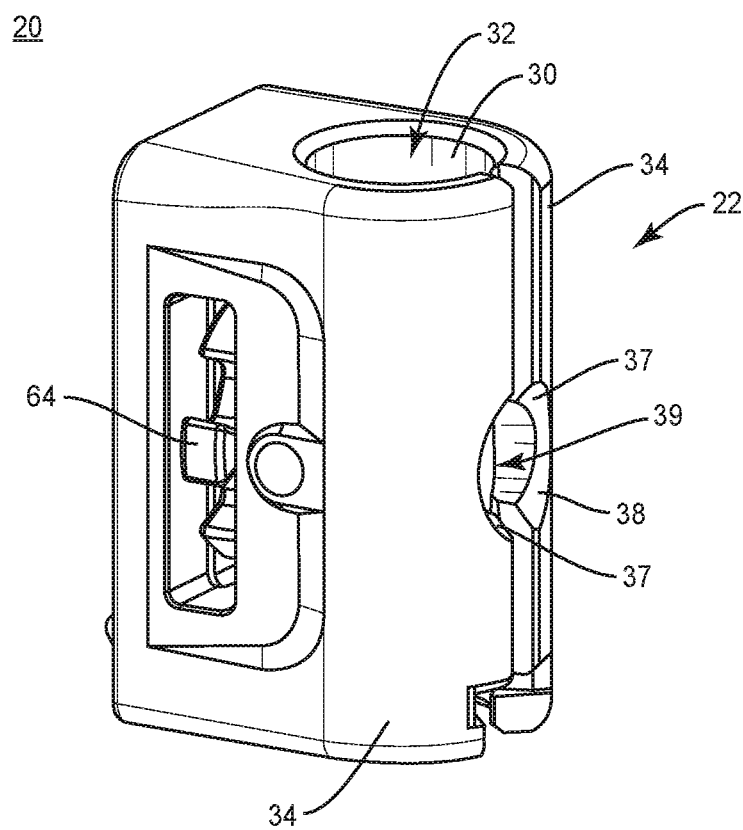
FIG. 2 is a perspective view of components of the system shown in FIG. 1.

End effector 20 includes a body 22. Body 22 includes spaced apart arms 34. Arms 34 extend axially along body 22, as shown in FIG. 2. Arms 34 each include a surface 30 that defines a channel 32. Channel 32 is configured for passage of a spinal construct and/or a surgical instrument, such as, for example, a surgical driver 100, as described herein. In some embodiments, arms 34 are flexible to facilitate insertion of the spinal construct and/or the surgical instrument. In some embodiments, each arm 34 includes a countersunk surface 37 that defines a recess 38. Recesses 38 form a passageway 39 to provide access to a connector, such as, for example, a clamp screw 36, as described herein. Passageway 39 is configured to guide and/or direct insertion of a surgical instrument, such as, for example, a screw driver 150 laterally through channel 32 to torque, drive or otherwise engage screw 36 to connect end effector 20 with robotic arm 14, as described herein.

Figure 3:
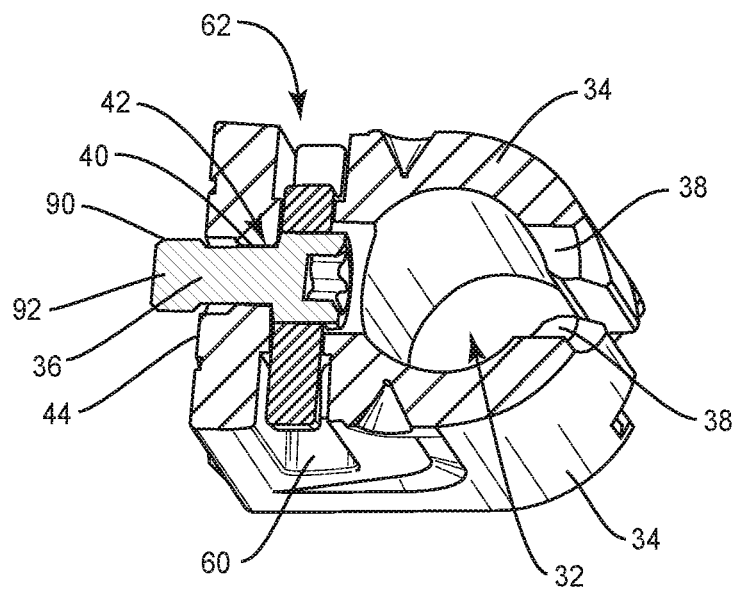
FIG. 3 is a cutaway view of the components shown in FIG. 2.
Figure 6:
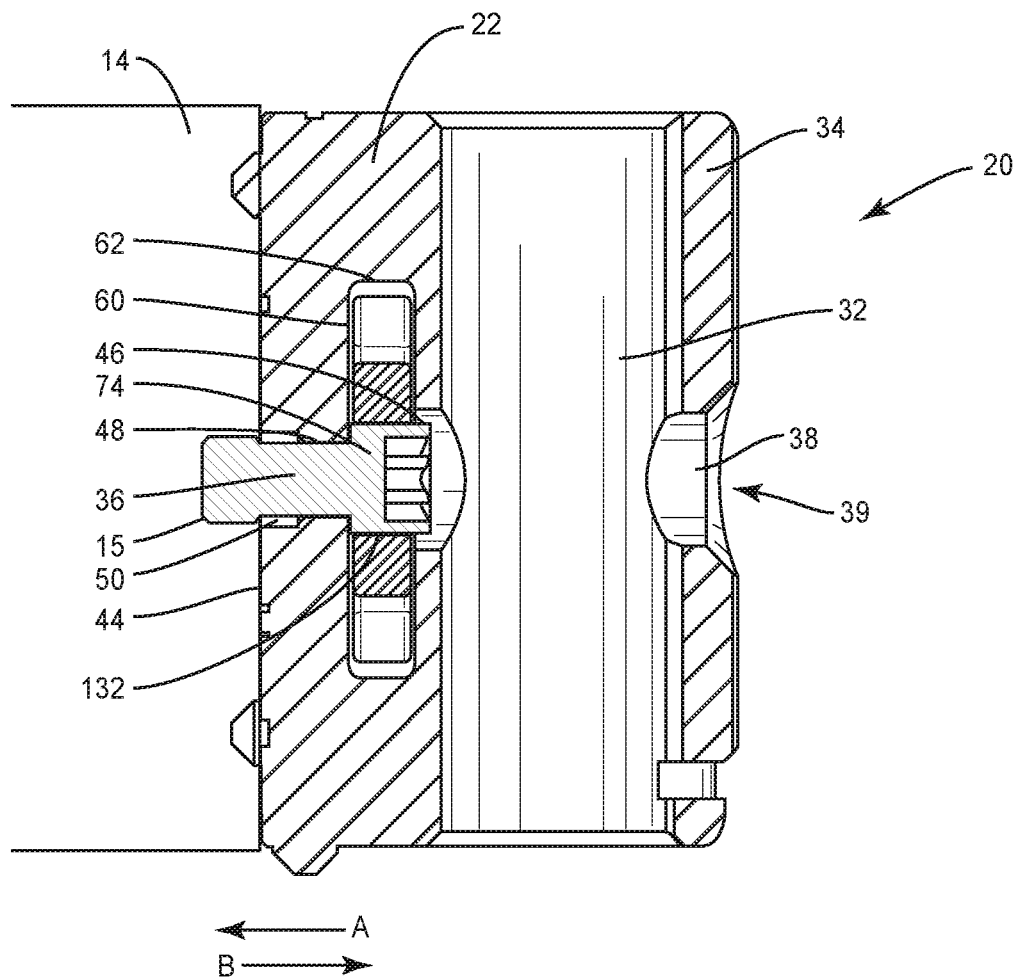
FIG. 6 is a cross section view of components of the system shown in FIG. 1.

Body 22 includes a surface 40 that defines an opening 42. Opening 42 extends from surface 30 to a surface 44 of body 20, as shown in FIG. 3. Opening 42 is disposed in communication with channel 32 such that screw 36 can be accessed through a portion of channel 32 for engagement with driver 150, as described herein. Opening 42 is configured for translation of screw 36, in the directions shown by arrows A and B in FIG. 6. Opening 42 includes a portion 46, a portion 48 and a portion 50. Portion 46 is disposed in communication with channel 32 such that screw 36 can be accessed through channel 32, as shown in FIG. 6. Portion 46 is configured for disposal of a head 74 of screw 36, as described herein.

Portion 48 is disposed between portion 46 and portion 50. Portion 48 is configured for disposal of a shaft 80 of screw 36. Portion 50 is disposed in communication with surface 44 of body 22, as shown in FIG. 6. Portion 50 is configured for disposal of a mating portion 90 of shaft 80. Portion 50 includes a wall 52 that defines a depth X1 of portion 50. Wall 52 is configured to limit translation of screw 36 during disengagement of screw 36 from robotic arm 14, for example, as screw 36 translates, in the direction shown by arrow A in FIG. 6, as described herein. Wall 52 limits, resists and/or prevents translation of screw 36 to maintain engagement of head 74 with the release, as described herein.

Portions 46, 48, 50 are disposed in axial alignment. Portions 46, 48, 50 include diameters configured to accommodate various sizes of portions of screw 36. Opening 42 is disposed lateral to channel 32. In some embodiments, opening 42 is disposed at alternate orientations relative to channel 32, such as, for example, at transverse, perpendicular and/or other angular orientations such as acute or obtuse, and/or may be offset or staggered.

Body 22 includes a surface 60 that defines a slot 62. Slot 62 is configured for disposal of the release, such as, for example, a wheel 64, as described herein. Slot 62 is disposed in communication with portion 46 of opening 42 such that screw 36 is engaged with wheel 64, as shown in FIGS. 3-6. Slot 62 includes a square cross section configuration. In some embodiments, slot 62 may have various configurations including, for example, round, oval, polygonal, irregular, consistent, variable, uniform and non-uniform.

Figure 5:
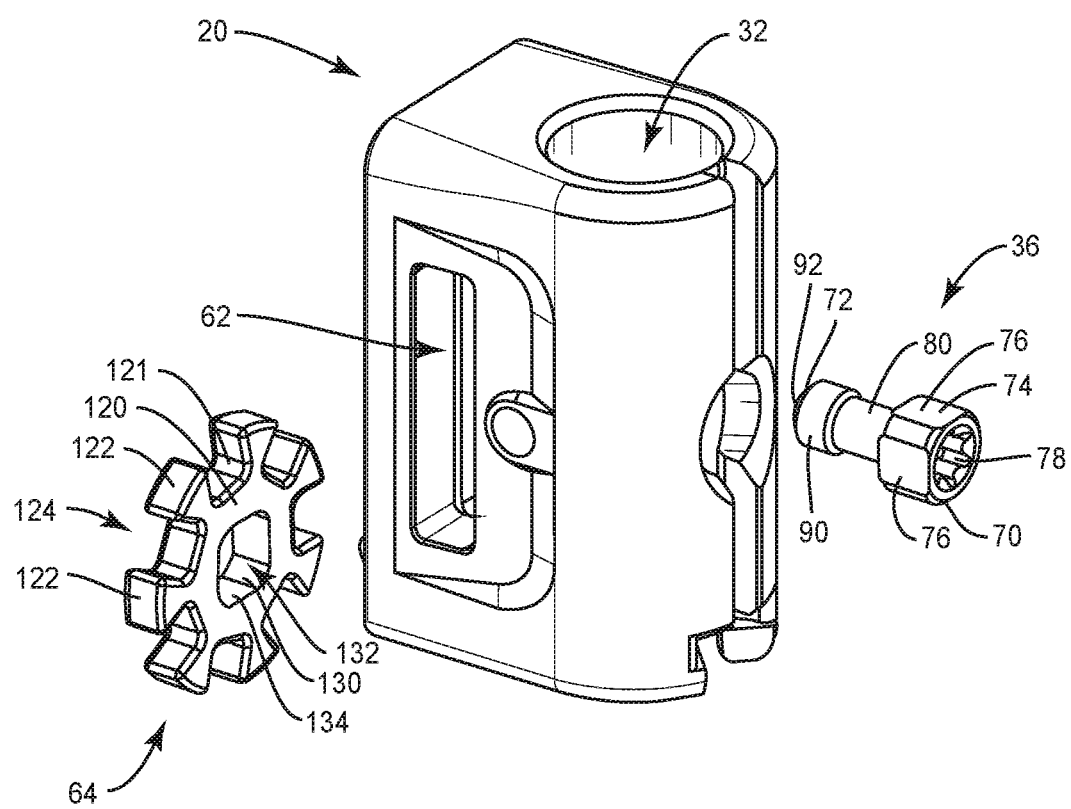
FIG. 5 is a perspective view of the components shown in FIG. 2, with parts separated.

Screw 36 extends between an end 70 and an end 72, as shown in FIG. 5. In some embodiments, screw 36 is configured as a clamp screw. Screw 36 is configured to engage a corresponding mating surface 15 of robotic arm 14, to connect end effector 20 with robotic arm 14. Screw 36 includes a head 74. Head 74 is configured for engagement with a portion of wheel 64 such that rotation of wheel 64 simultaneously rotates screw 36 to disengage screw 36 from robotic arm 14, as described herein. In some embodiments, head 74 includes planar surfaces 76 configured for a keyed connection with wheel 64.

Head 74 includes a socket 78. Socket 78 is configured for engagement with driver 150 to drive, torque or otherwise connect screw 36 with robotic arm 14 to assemble end effector 20 with robotic arm 14, as described herein. In some embodiments, socket 78 includes a hexalobe geometry for a mating engagement with a correspondingly portion of driver 150. In some embodiments, socket 78 can alternatively include a cruciform, phillips, square, hexagonal, polygonal, star cross sectional configuration for disposal of a correspondingly shaped portion of driver 150. Screw 36 includes shaft 80 the extends from head 74.

Screw 36 includes mating portion 90 disposed with shaft 80 at end 72. Mating portion 90 includes a surface 92 that is configured for engagement with a portion of robotic arm 14. In some embodiments, surface 92 includes a threaded surface configured for engagement with a threaded surface of robotic arm 14 to facilitate connection of end effector 20 with robotic arm 14. For example, as surface 92 engages a corresponding mating surface 15 of robotic arm 14, screw 36 draws and/or pulls end effector 20 into connection with robotic arm 14.

Figure 8:
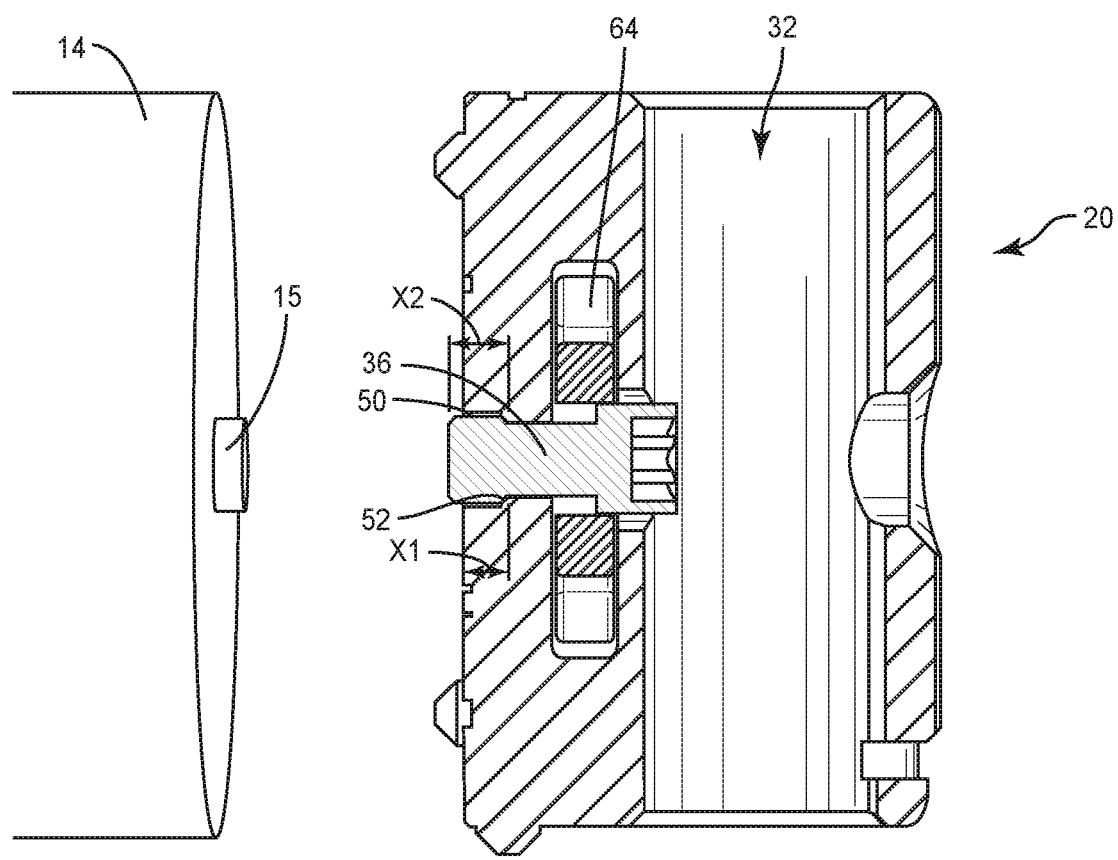
FIG. 8 is a perspective view, in part cross section, of components of the system shown in FIG. 1, with parts separated.

Mating portion 90 includes a length X2. Length X2 is greater than depth X1 of portion 50. For example, length X2 is 1 mm greater than depth X1 such that mating portion 90 protrudes from surface 50 approximately 1 mm, as shown in FIG. 8. In some embodiments, this configuration facilitates engagement of mating portion 90 with robotic arm 14.

Figure 4:
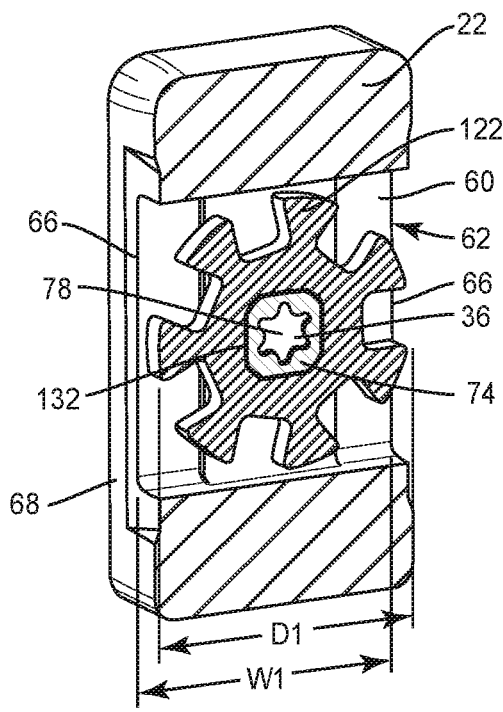
FIG. 4 is a cutaway view of the components shown in FIG. 2.

Wheel 64 includes a body 120. Body 120 includes a surface 121. A plurality of radial members, such as, for example, arms 122 extend from surface 121. Arms 122 define a recess 124 disposed between adjacent arms 122. Recess 124 is configured for disposal of a surgical instrument, such as, for example, driver 150 to actuate movement, for example, rotation of wheel 64. Wheel 64 is configured to be actuated for rotation within slot 62. Arms 122 extend a distance from surface 121 defining a diameter D1 of wheel 64. Surface 60 of slot 62 includes edges 66 extending along an outer surface 68 of body 22, as shown in FIG. 4. Edges 66 define a width W1 of slot 64.

In some embodiments, diameter D1 is less than width W1 such that arms 122 are disposed within slot 62 to resist and/or prevent accidental rotation of wheel 64. In some embodiments, diameter D1 is equal to width W1 such that arms 122 are disposed in a flush orientation with edges 66 to resist and/or prevent accidental rotation of wheel 64.

Body 120 includes a surface 130. Surface 130 defines a mating portion, for example, an opening 132. Opening 132 is configured for disposal of head 74. Engagement of head 74 with surface 130 facilitates simultaneous rotation of wheel 64 and screw 36. In some embodiments, surface 130 defines planar surfaces, for example, flats 134 configured for engagement with surfaces 76 of head 74 in a keyed connection.

Figure 7:
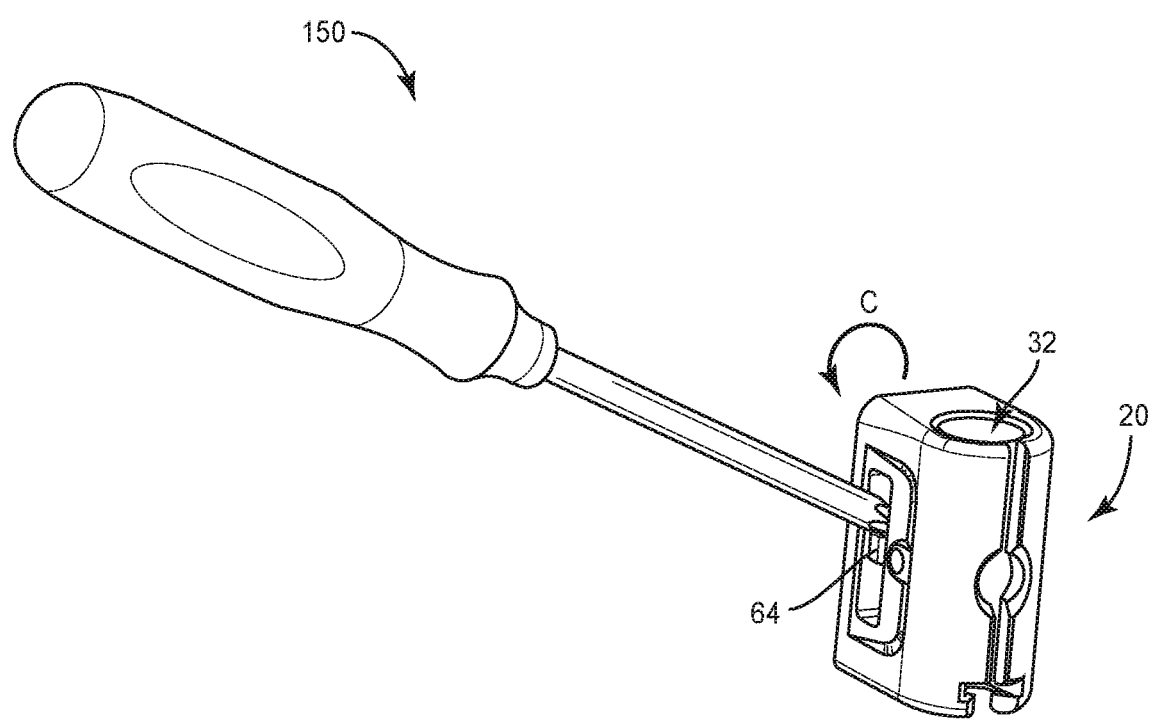
FIG. 7 is a perspective view of components of one embodiment of a surgical system in accordance with the principles of the present disclosure.

In use, driver 150 is engaged with socket 78. Driver 150 is manipulated to rotate screw 36 into engagement with robotic arm 14. Screw 36 pulls and/or draws end effector 20 for connection with robotic arm 14, as shown in FIG. 6. Driver 100 is disposed with channel 32. In some embodiments, during use, driver 100 may become fixed, frictionally fixed, stuck, galled and/or jammed with surface 30 of end effector 20 thereby preventing access to socket 78. As such, screw 36 cannot be disengaged from robotic arm via socket 78. To disconnect end effector 20 from robotic arm 14, wheel 64 is actuated by insertion of driver 150 between arms 122, as shown in FIG. 7. Driver 150 is utilized as a lever to apply a force to arm 122 causing wheel 64 to rotate, in a direction shown by arrow C in FIG. 7. Wheel 64, via engagement of surfaces 76, 130, causes screw 36 to rotate out of engagement with robotic arm 14, as shown in FIG. 8. Wall 52 of portion 50 limits, resists and/or prevents translation of screw 36 out of engagement with wheel 64 to maintain a connection between wheel 64 and screw 36.

In assembly, operation and use, surgical system 10, similar to the systems and methods described herein, is employed with a surgical procedure, such as, for example, a treatment of an applicable condition or injury of an affected section of a spinal column and adjacent areas within a body. In some embodiments, one or all of the components of surgical system 10 can be delivered or utilized as a pre-assembled device or can be assembled in situ. Surgical system 10 may be completely or partially revised, removed or replaced.

In use, to treat vertebrae (not shown), a medical practitioner obtains access to a surgical site in any appropriate manner, such as through incision and retraction of tissues. In some embodiments, surgical system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

In connection with the surgical procedure, end effector 20 is assembled with robotic arm 14. Driver 150 is inserted through passageway 39 into engagement with socket 78 of screw 36. Driver 150 is engaged with socket 78. End effector 20 is positioned adjacent robotic arm 14. Driver 150 is manipulated to rotate screw 36 into engagement with mating surface 15 of robotic arm 14. Screw 36 pulls and/or draws end effector 20 into connection with robotic arm 14, as shown in FIG. 6.

A bone fastener is connected with driver 100. Driver 100 is inserted into channel 32 for disposal adjacent the surgical site. Driver 100 is manipulated via robotic arm 14 to torque, drive or otherwise engage the bone fastener with tissue. During use, manipulation of driver 100 may cause a surface of driver 100 to become fixed, frictionally fixed, stuck, galled and/or jammed with end effector 20 requiring the removal of end effector 20 from robotic arm 14.

Fixation of driver 100 with end effector 20 prevents access to socket 78 of screw 36 to disengage end effector 20 from robotic arm 14. Wheel 64 is utilized to disconnect end effector 20 from robotic arm 14. Driver 150 is inserted between arms 122 to apply a leveraging force to actuate wheel 63, as shown in FIG. 7. Driver 150 applies a force to arm 122 causing wheel 64 to rotate, in a direction shown by arrow C in FIG. 7. Surfaces 130 engage surfaces 76 causing screw 36 to rotate out of engagement with robotic arm 14 to remove end effector 20 and driver 100 that was fixed, frictionally fixed, stuck, galled and/or jammed within end effector 20, as shown in FIG. 8. In some embodiments, an alternate end effector 20 can be attached to robotic arm 14.

Upon completion of a procedure, the surgical instruments and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical guide comprising:
   a body including an inner surface defining a cavity configured for disposal of a surgical instrument, the body further defining an opening communicating with the cavity, the body including spaced apart arms, the arms defining an axial channel;
   a connector disposable with the opening and engageable with a surgical robot; and
   a release engageable with the connector, the release including flats configured for a keyed connection with the connector, the flats defining a substantially square hole, the connector comprising a head and a shaft extending from the head, the head being disposed in the hole such that an outer surface of the head directly engages the flats.

2. A surgical guide as recited in claim 1, wherein the opening is disposed lateral to the cavity.

3. A surgical guide as recited in claim 1, wherein the opening includes a first portion, a second portion and a third portion.

4. A surgical guide as recited in claim 3, wherein the portions are axially aligned.

5. A surgical guide as recited in claim 1, wherein the connector includes a clamp screw.

6. A surgical guide as recited in claim 1, wherein the shaft is configured for connection with the surgical robot.

7. A surgical guide as recited in claim 1, wherein the connector includes a mating surface configured for connection with the surgical robot.

8. A surgical guide as recited in claim 1, wherein the connector is moveable within the opening for a range of engagement with the release.

9. A surgical guide as recited in claim 1, further comprising a slot disposed in communication with a portion of the opening.

10. A surgical guide as recited in claim 9, wherein the slot is configured for disposal of the release.

11. A surgical guide as recited in claim 1, wherein the release is engageable with the connector to facilitate disengagement of the connector from the surgical robot.

12. A surgical guide as recited in claim 1, wherein the release includes a rotatable wheel.

13. A surgical guide as recited in claim 1, wherein the release includes a plurality of radial members.

14. A surgical guide comprising:
    a robotic arm including an inner surface defining a channel configured for disposal of a surgical instrument, the robotic arm further defining an opening communicating with the channel, the robotic arm including spaced apart arms, the arms defining an axial channel;
    a screw disposable with the opening and engageable with a surgical robot; and
    a rotatable wheel engageable with the screw, the wheel including flats configured for a keyed connection with the screw, the flats defining a substantially square hole, the screw comprising a head and a shaft extending from the head, the head being disposed in the hole such that an outer surface of the head directly engages the flats.

15. A surgical guide as recited in claim 14, further comprising a slot disposed in communication with a portion of the opening.

16. A surgical guide as recited in claim 15, wherein the slot is configured for disposal of the rotatable wheel.

17. A surgical guide comprising:
    a body including an inner surface defining a cavity configured for disposal of a surgical instrument, the body further defining an opening communicating with the cavity and a slot in communication with the opening, the body including spaced apart arms, the arms defining an axial channel;
    a connector disposable with the opening and engageable with a surgical robot;
    and a wheel disposable with the slot and engageable with the connector, the wheel including flats configured for a keyed connection with the connector, the flats defining a substantially square hole, the connector comprising a head and a shaft extending from the head, the head being disposed in the hole such that an outer surface of the head directly engages the flats.

* * * * *